(12) United States Patent
Ungemach et al.

(10) Patent No.: US 7,290,548 B2
(45) Date of Patent: Nov. 6, 2007

(54) REINFORCED THERMOPLASTIC PATIENT RESTRAINTS FOR RADIATION THERAPY

(75) Inventors: Robert Ungemach, Elm Grove, WI (US); Jeffrey S. Nibbelink, Sioux Center, IA (US)

(73) Assignee: MEDTEC, Inc., Orange City, IA (US)

( * ) Notice: Subject to any disclaimer, the term of this patent is extended or adjusted under 35 U.S.C. 154(b) by 0 days.

(21) Appl. No.: 10/523,504

(22) PCT Filed: Oct. 4, 2002

(86) PCT No.: PCT/US02/31816

§ 371 (c)(1),
(2), (4) Date: Jun. 6, 2005

(87) PCT Pub. No.: WO2004/032781

PCT Pub. Date: Apr. 22, 2004

(65) Prior Publication Data

US 2005/0229936 A1 Oct. 20, 2005

(51) Int. Cl.
*A61G 15/00* (2006.01)
*A61F 5/37* (2006.01)
*A61F 11/00* (2006.01)
*A61B 19/00* (2006.01)

(52) U.S. Cl. .................. 128/869; 128/845; 128/846; 128/857

(58) Field of Classification Search ............ 602/6, 602/7, 8; 128/845, 846, 849, 857, 869, 870
See application file for complete search history.

(56) References Cited

U.S. PATENT DOCUMENTS 5,370,117 A * 12/1994 McLaurin, Jr. ............... 5/622
5,531,229 A * 7/1996 Dean et al. ................. 128/866
5,566,681 A * 10/1996 Manwaring et al. .......... 5/622
5,595,191 A * 1/1997 Kirk .......................... 128/846
5,702,406 A * 12/1997 Vilsmeier et al. ........... 606/130

(Continued)

FOREIGN PATENT DOCUMENTS

EP          1 095 640 A1   5/2001
WO   PCT WO 97/02942       1/1997

OTHER PUBLICATIONS

12PP Med-Tec, Inc. 2002-2003 Product Catalog, "Uni-frame® head & neck immobilization system—Thermoplastic Masks" 1 page, 1999.

(Continued)

*Primary Examiner*—Patricia Bianco
*Assistant Examiner*—Kari Petrik
(74) *Attorney, Agent, or Firm*—Caesar, Rivise, Bernstein, Cohen & Pokotilow, Ltd.

(57) ABSTRACT

A patient restraint member is provided for medical procedures, such as radiation therapy. The restraint member is formed from a sheet of thermoplastic material that can be softened upon heating so as to be formable into a shape corresponding to a patient's body part to be restricted and setting upon cooling to retain the shape. The sheet includes spaced apart groups of perforations which minimize shrinkage during the formation process. The sheet also includes solid bands extending between the groups of perforation to provide rigidity and strength to the formed sheet.

17 Claims, 8 Drawing Sheets

U.S. PATENT DOCUMENTS

| | | | |
|---|---|---|---|
| 5,775,337 A * | 7/1998 | Hauger et al. | 128/869 |
| 5,800,353 A * | 9/1998 | McLaurin, Jr. | 600/407 |
| 5,848,449 A * | 12/1998 | Hauger et al. | 5/637 |
| 6,161,237 A * | 12/2000 | Tang et al. | 5/621 |
| 6,376,846 B2 * | 4/2002 | Livingston | 250/492.1 |
| 6,945,251 B2 * | 9/2005 | Woodburn, III | 128/857 |
| 2002/0038659 A1 * | 4/2002 | Al-Kassim | 128/845 |
| 2004/0159325 A1 * | 8/2004 | Korver et al. | 128/869 |

OTHER PUBLICATIONS

Head & Mask brochure; "Patient Positioning & Immobilization" "Composite Thermoplastic", 1 page, 1999.

"The BrainLAB Mask System for Stereotactic and High Precision Treatments" BrainLAB Info pamphlet.

"Mark System for SRT" http://www.brainlab.com/scripts/website_full_story.asp?article_id=621&article_type=69&return=cms . . . Sep. 26, 2002 (1 page).

"Klarity® Designed for maximum patient comfort and positioning accuracy" http://www.bionixusa.com/Pages/KlarityPage.html; Sep. 26, 2002 (1 page).

Radiation Oncology, Nuclear Associates Diagnostic Radiology and Radiation Oncology Catalog (4 pages).

* cited by examiner

REINFORCED THERMOPLASTIC PATIENT RESTRAINTS FOR RADIATION THERAPY

BACKGROUND OF THE INVENTION

Thermoplastic sheets are well known for use in the field of radiation therapy treatment, including Intensity Modulated Radiation Therapy (IMRT). Typically, such thermoplastic sheets are heated and then formed to a shape corresponding to the body part to be restrained, such as a mask for restraining a patient's head. The sheet is mounted on a frame which can be secured to a treatment table to facilitate proper positioning of the patient on the table for radiation treatment.

The prior art thermoplastic sheets are solid sheets or perforated sheets. Solid thermoplastic sheets require much higher forces to form, retain much more heat and tend to have excess shrinkage when formed to the body shape, all of which leads to patient discomfort. The perforations serve to reduce the force necessary to form, minimize the heat transferred to the patient, and minimize shrinkage of the thermoplastic material. When the sheet is formed into a facemask, the holes permit a patient to see and breathe through the sheet, and thereby minimize or eliminate claustrophobic feelings. The holes can be punched into the sheet, or formed when the sheet is made in an injection molding process. However, totally perforated sheets do not offer the necessary rigidity which is present in a solid or non-perforated sheet.

Accordingly, a primary objective of the present invention is the provision of an improved thermoplastic sheet for use in medical procedures, including IMRT.

Another objective of the present invention is the provision of an improved thermoplastic sheet having perforations and non-perforated reinforcing bands.

Further objective of the present invention is the provision of an improved perforated thermoplastic sheet with enhanced rigidity.

Another objective of the present invention is the provision of an improved thermoplastic sheet which is sufficiently rigid, and which avoids excess shrinkage.

A further objective of the present invention is the provision of an improved thermoplastic sheet, which is comfortable when used on a patient for medical procedures.

These and other objectives will become apparent from the following invention.

BRIEF SUMMARY OF THE INVENTION

The improved thermoplastic sheet of the present invention is intended for use as a patient restraint member in medical procedures such as radiation therapy treatment, including IMRT. The sheet may take various forms and shapes to restrain various body parts, including the head, neck, breasts, and hips/pelvic area. The sheet includes a plurality of groups of perforations to increase patient comfort with non-perforated bands extending between the groups of perforation to provide enhanced rigidity. The perforations also minimize shrinkage of the sheet when it is heated, formed, and cooled into a set shape corresponding to the body part to be restrained. The perimeter edge of the sheet is free from perforations. The solid bands extend inwardly from the perimeter edge of the sheet The bands may extend completely or partially across the sheet The solid bands are placed in strategic areas to provide increased rigidity while the perforations minimize shrinkage. The perforations may be punched or formed during injection molding.

DETAILED DESCRIPTION OF THE INVENTION

Figure 1:
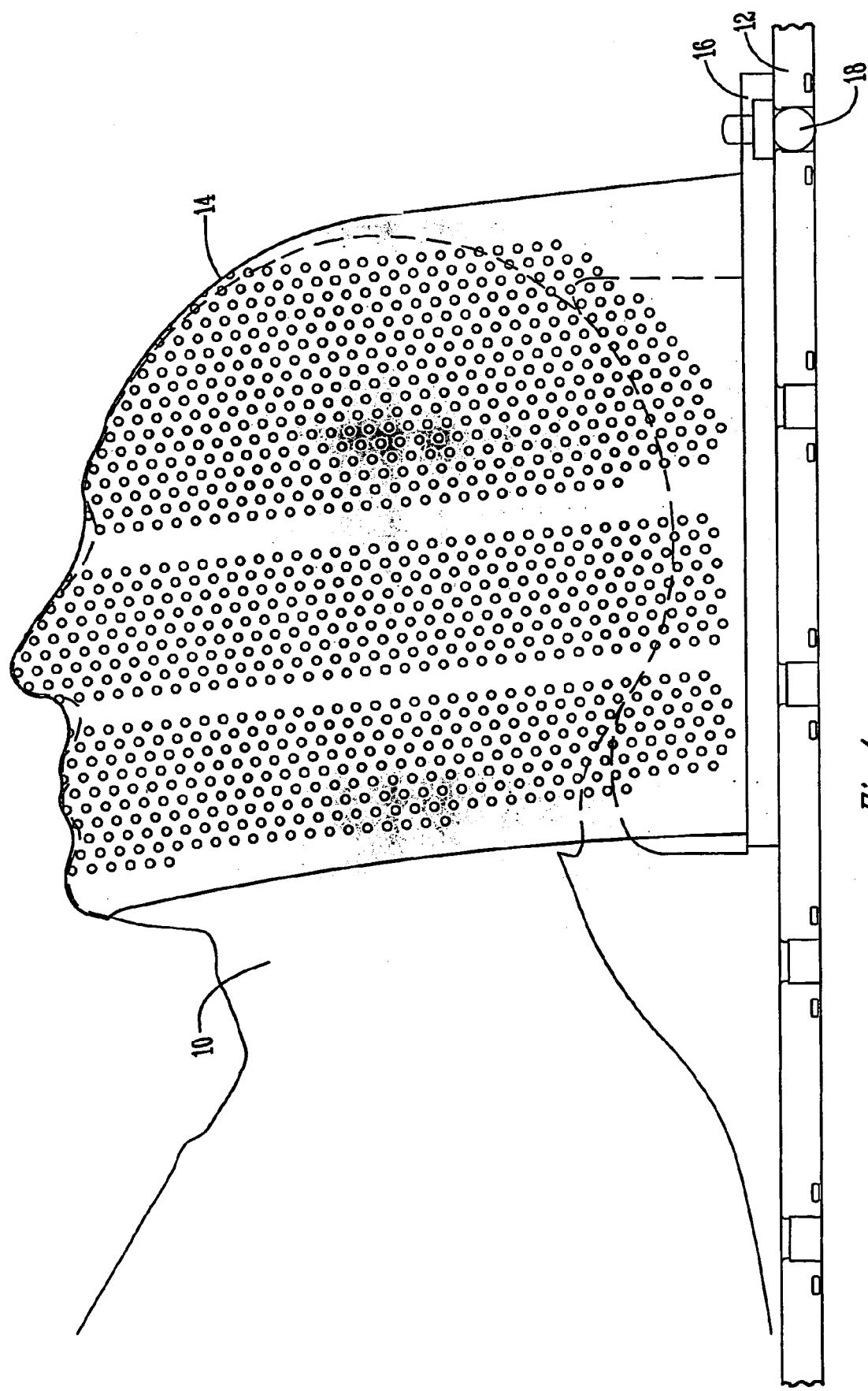
FIG. 1 is a side elevation view of a thermoplastic sheet formed into a mask for restraining a patient's head and mounted onto a radiation treatment table.
Figure 2:
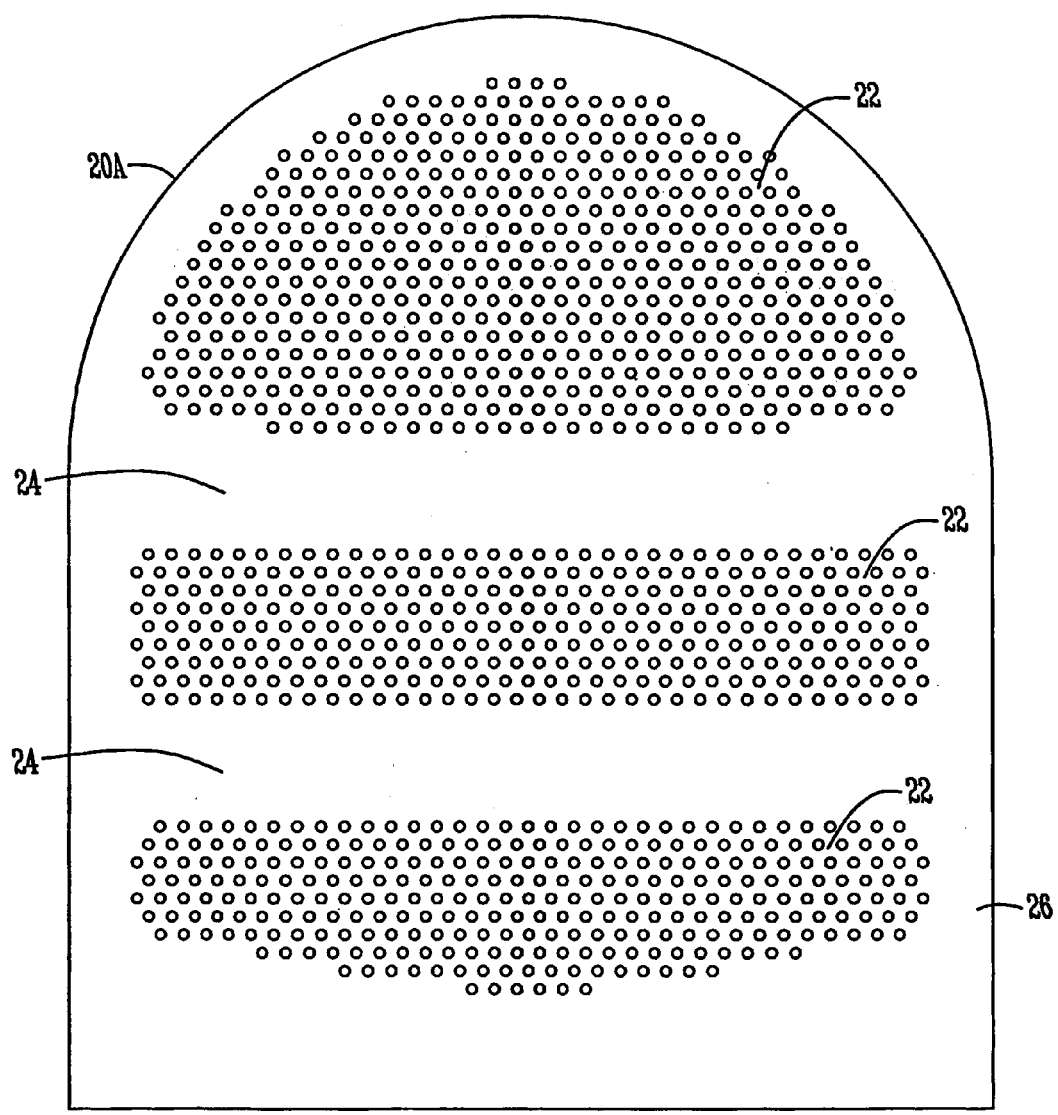
FIGS. 2–5 are each a top plan view of a sheet adapted to be formed into a head restraint, and showing various alternative embodiments of the perforation groupings and solid reinforcing bands, according to the present invention.
Figure 3:
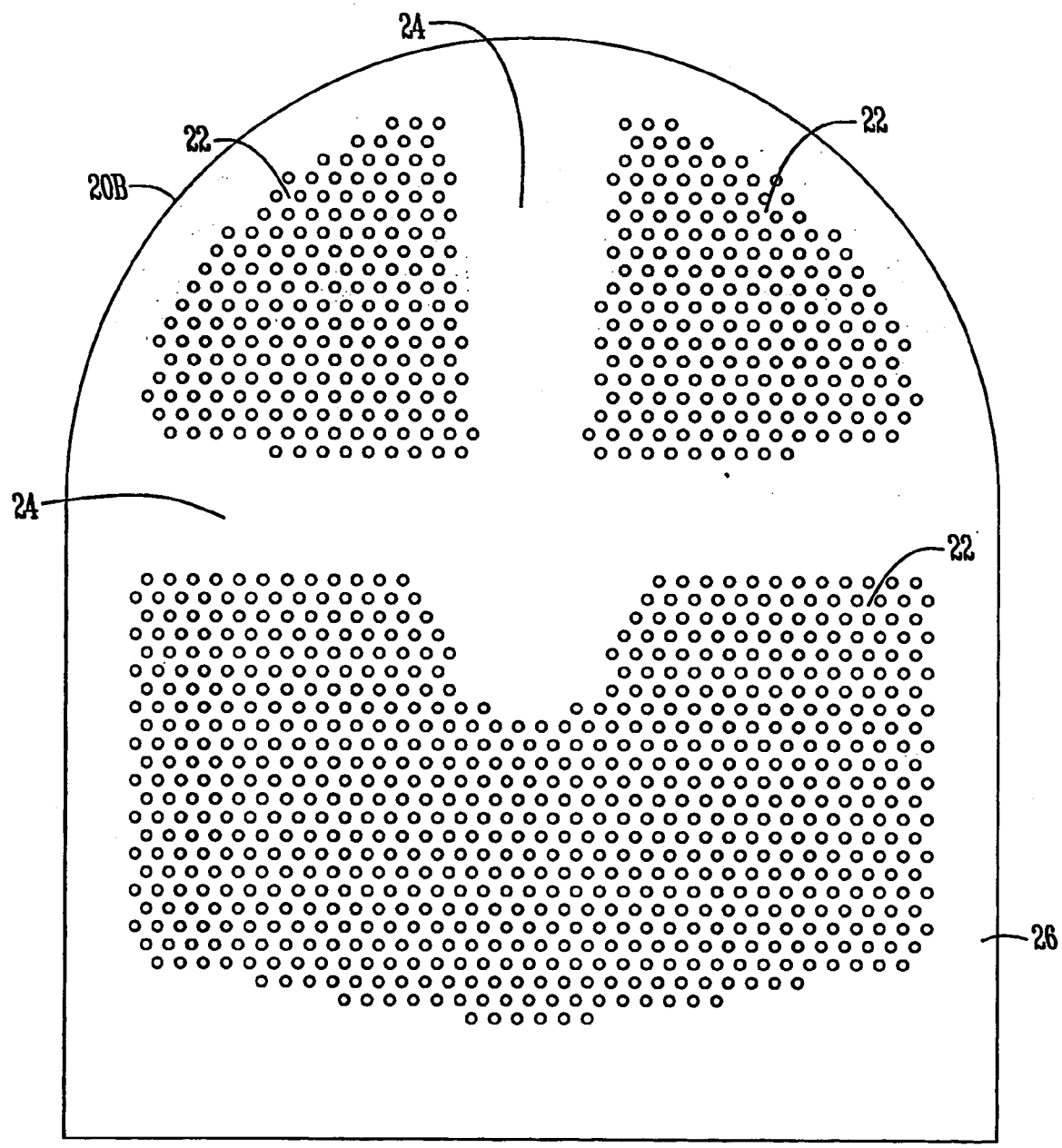
Figure 4:
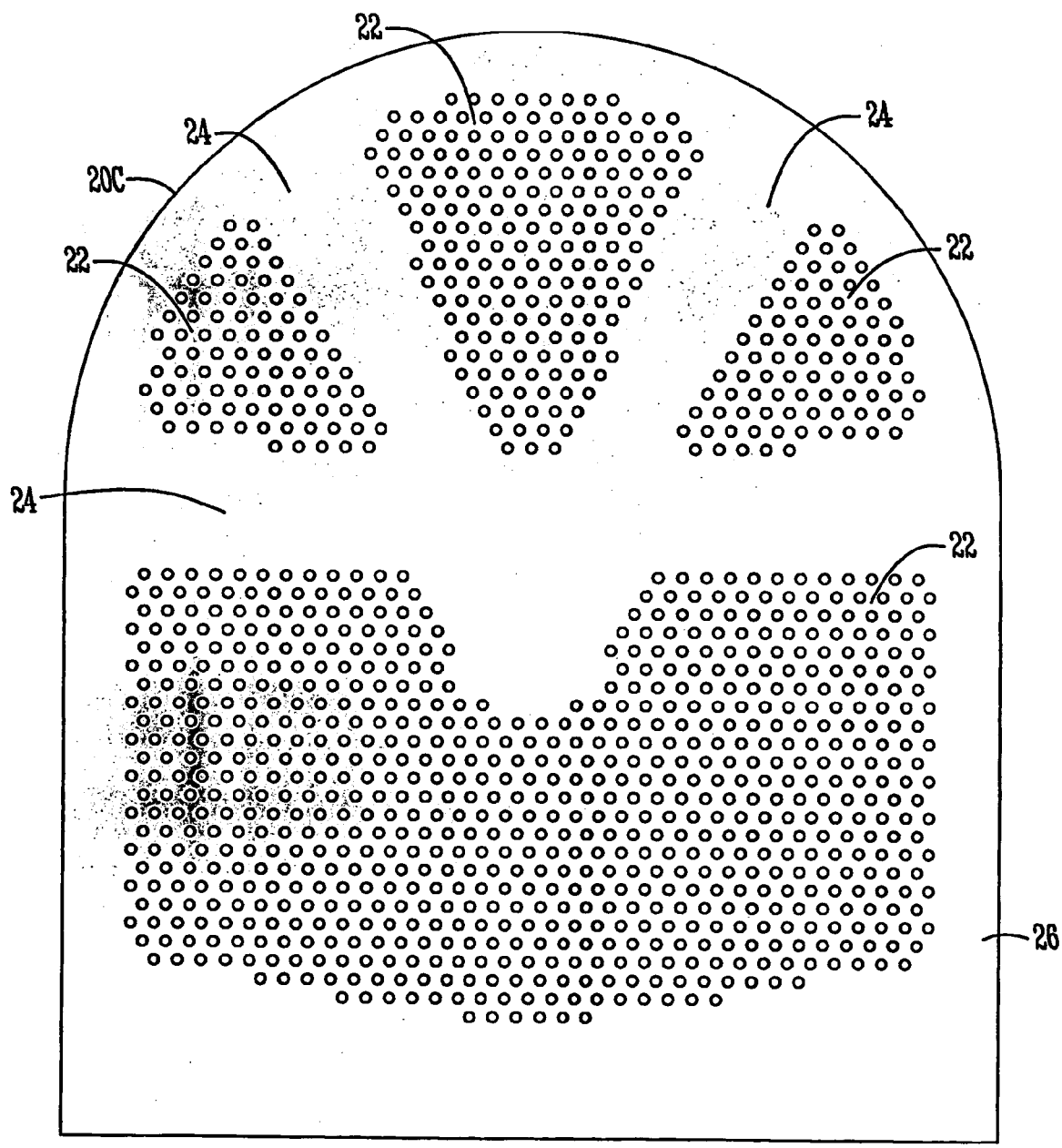

In FIG. 1 a patient 10 as shown on a treatment table 12 in preparation for radiation therapy on his/her head. The patient's head is restrained by a thermoplastic mask 14, which has been formed to fit the patient's head. The mask 14 is mounted on a frame 16, which is adapted to be secured to the treatment table 12 in any convenient manner. For example, the table 12 may include a plurality of indexing notches adapted to receive an indexing member 18 extending from the frame 16, as described in the U.S. Pat. No. 6,161,237.

Figure 5:
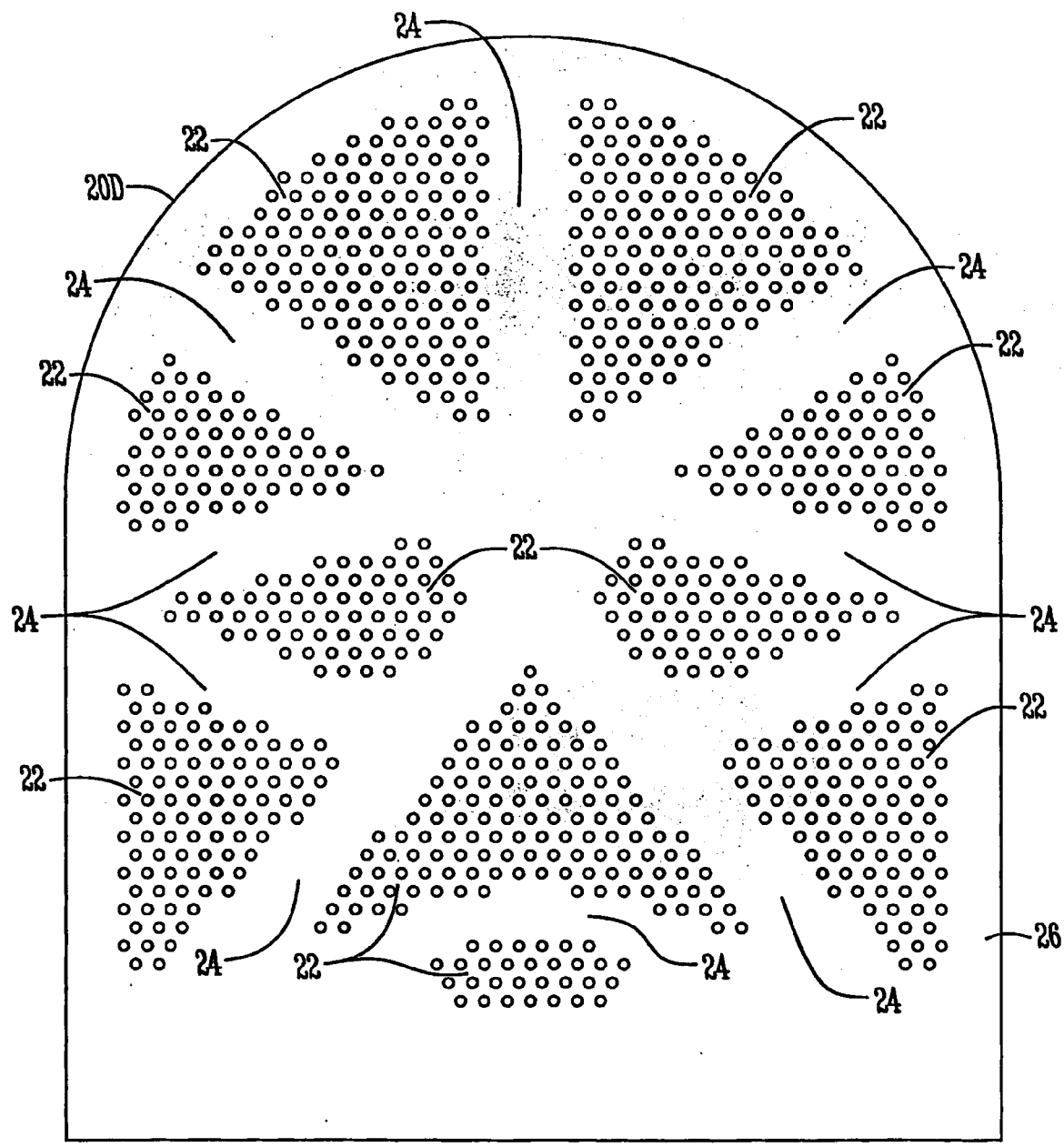
Figure 9:
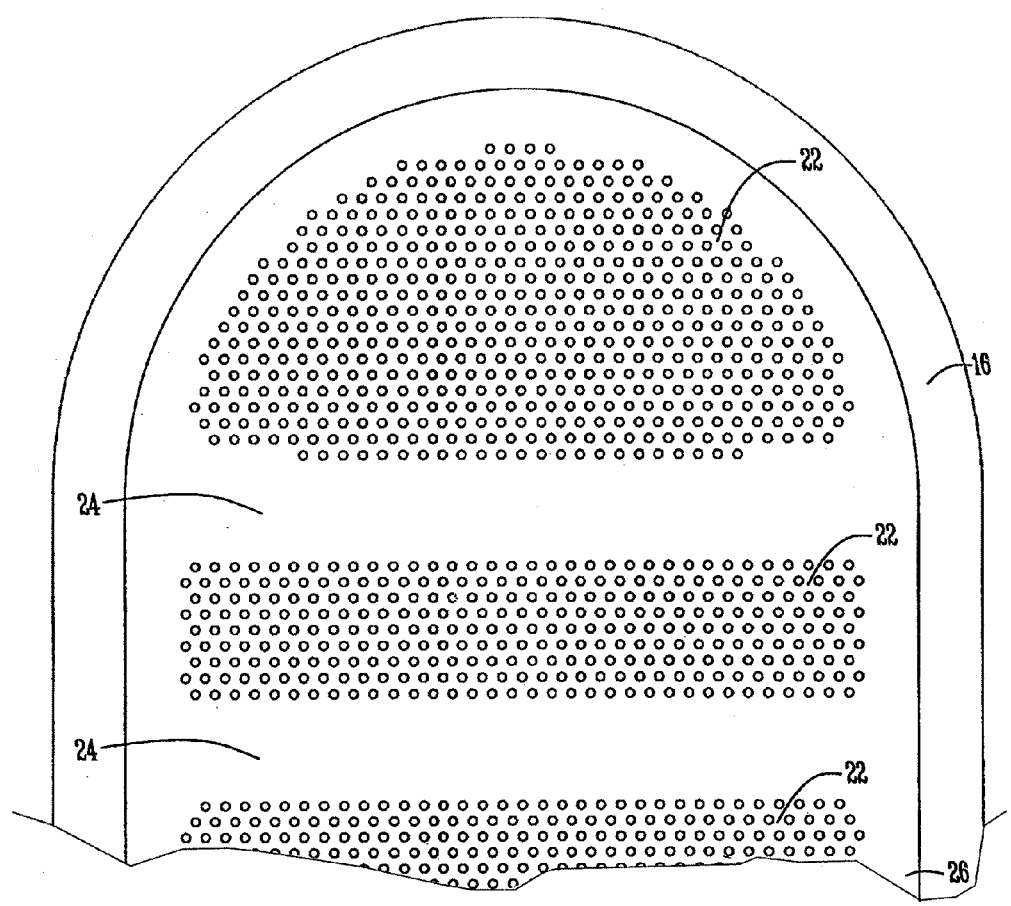
FIG. 9 is a top plan view of a portion of the thermoplastic sheet and associated U-shaped frame that is shown in FIG. 1.

The mask 14 is formed from one of the thermoplastic sheets 20A–20D shown in FIGS. 2–5, respectively. Each sheet 20 includes spaced apart groups of perforations or holes 22 extending through, or partially through, the sheets 20A–20D. The spacing between the groups of the holes define solid bands 24 which increase the rigidity of the sheets 20A–20D, and thus the mask 14. The holes 22 minimize shrinkage of the sheets during the mask formation process. Each of the sheets 20A–D has a non-perforated perimeter edge 26 for seducement of the sheet to the U-shaped frame 16 (FIGS. 1 and 9). Alternatively, the groups of holes 22 may extend to the edge of the sheet 20A–D, which facilitates bonding of the sheet 20A–D to the frame 16, for example using adhesives or heat. The non-perforated bands 24 extend inwardly from the perimeter edge 26 of the sheets 20A–D. Some bands 24 may extend completely across the sheets 20A–D while other bands 24 extend partially across the sheets. Also, the bands 24 may extend perpendicularly to the opposite side edges, top edge, or bottom edge, or angularly thereto in a non-perpendicular orientation. As seen in FIG. 5, some of the bands may criss-cross the sheet 20D. The holes 22 may be formed by punching or during an injection process used to make the sheets 20A–D.

Figure 6:
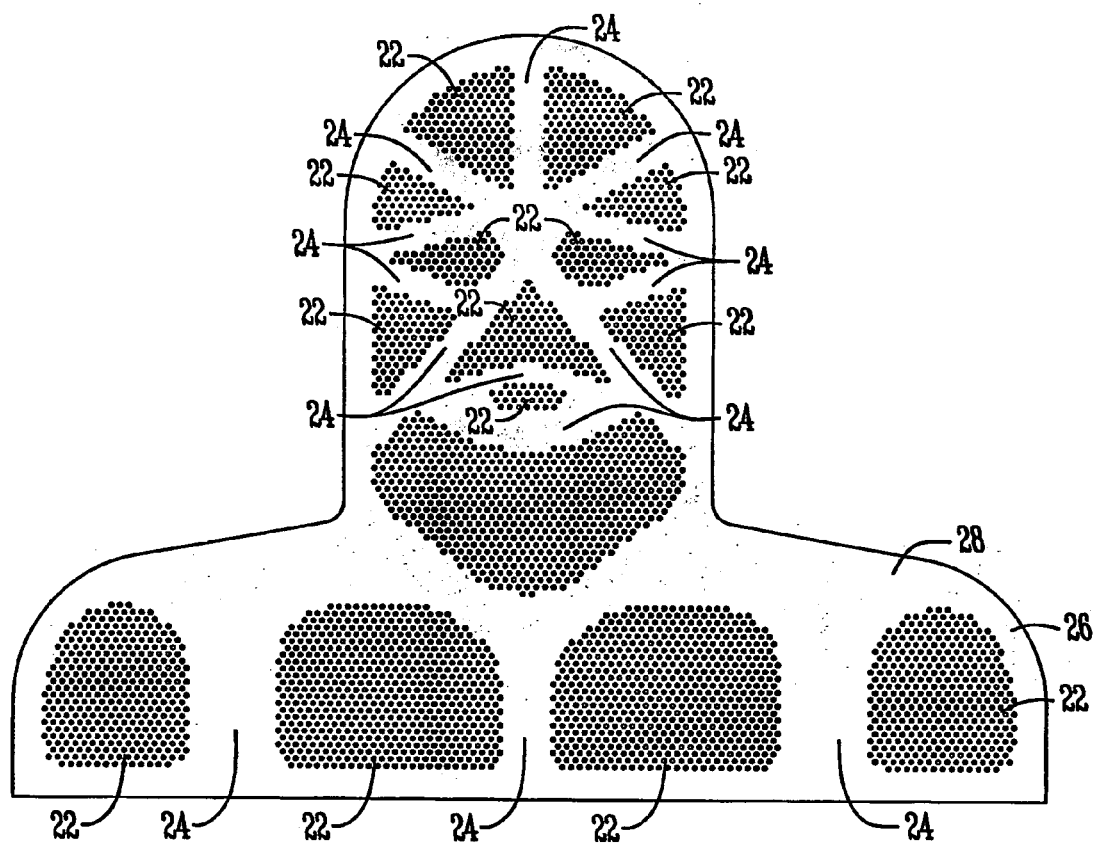
FIG. 6 is a top plan view of a thermoplastic sheet adapted to be formed into a head and shoulder restraint with the perforations and reinforcing bands of the present invention.

FIG. 6 shows another sheet 28 adapted to be formed for restraining the head and shoulders of a patient. The holes 22 in the sheet 28 minimize shrinkage, while the solid bands 24 provide increased rigidity for the sheet 28 after it is heated, formed, and cooled to the set shape.

Figure 7:
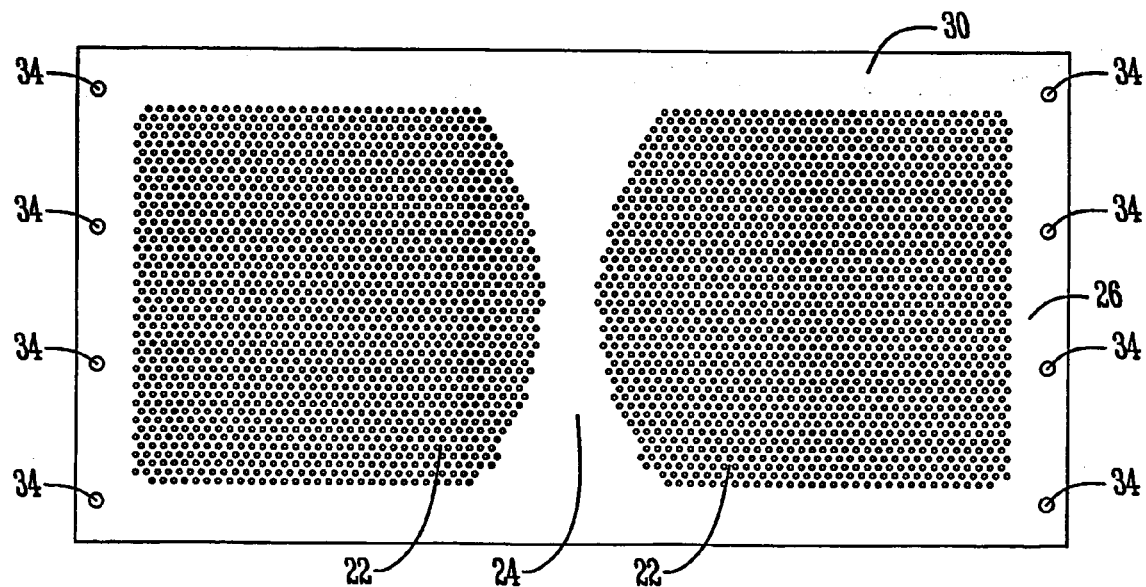
FIG. 7 is a top plan of a thermoplastic sheet adapted to be formed into a breast restraint with the perforations and reinforcing band of the present invention.
Figure 8:
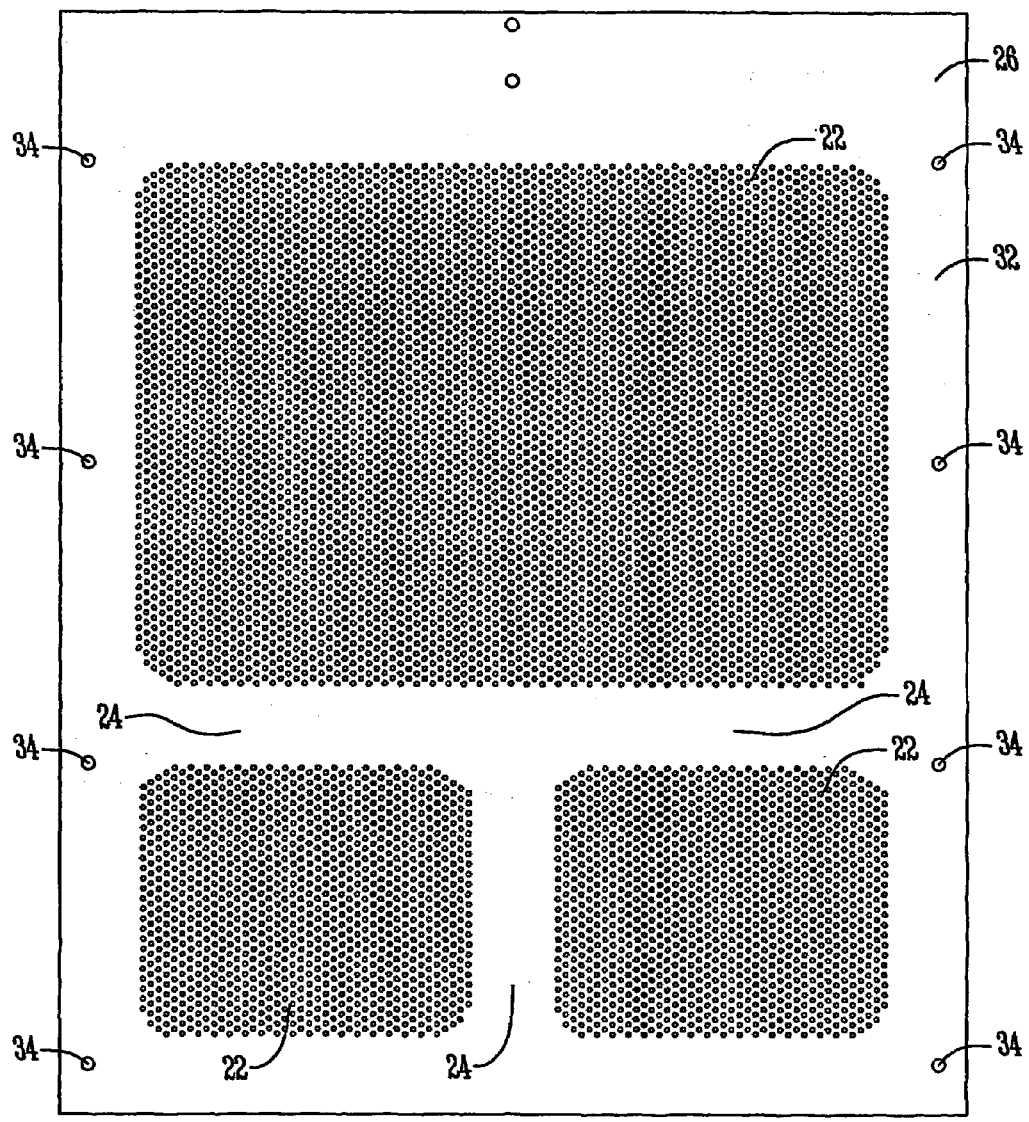
FIG. 8 is a top plan view of a thermoplastic sheet adapted to be formed into a hip/pelvic restraint and having the perforations and reinforcing bands of the present invention.

FIG. 7 shows another embodiment of the present invention where in a sheet 30 having holes 22 and a solid band 24 is adapted for formation and use in restraining the upper torso of a patient, for example, in breast radiation treatment. Similarly, FIG. 8 shows a thermoplastic sheet 32 with holes 22 and solid bands 24 according to the present invention. The sheet 32 is adapted to be formed and used as a hip/pelvic restraint. The enlarged holes 34 along the edges of the sheets 30 and 32 are used for attaching the sheets 30, 32 to a frame (not shown) which is then mounted to the treatment table.

Whereas the invention has been shown and described in connection with the preferred embodiment thereof, it will be understood that any modifications, substitutions, and additions may be made which are within the intended broad scope of the following claims. From the foregoing, it can be seen that the present invention accomplishes at least all of the stated objectives.

What is claimed is:

1. A patient restraint member for use in medical procedures, comprising:
    an integral, unitary sheet having an inner surface and an outer surface, with only a single layer of material between those surfaces, said material being formed of a thermoplastic material that can be softened upon heating so as to be formable into a shape corresponding to a patient's body part to be restrained and setting upon cooling to retain the shape, the sheet having a perimeter edge lying in a common plane and with the inner surface of the sheet arranged to directly engage the patient's body part to restrain movement of the patient's body part;
    spaced apart groups of perforations in the sheet;
    non-perforated solid bands extending between the groups of perforations;
    a generally planar U-shaped frame arranged to be attached to and extending around a portion of the perimeter edge of the sheet and being coplanar with the perimeter edge.

2. The patient restraint member of claim 1 wherein the bands extend inwardly from the perimeter edge.

3. The patient restraint member of claim 2 wherein the bands intersect at a location spaced inwardly from the perimeter edge.

4. The patient restraint member of claim 2 wherein the bands extend perpendicular to the perimeter edge.

5. The patient restraint member of claim 2 wherein the bands extend in a non-perpendicular angle from the perimeter edge.

6. The patient restraint member of claim 2 wherein the bands extend completely across the sheet.

7. The patient restraint member of claim 1 wherein the perimeter edge is without perforations.

8. The patient restraint member of claim 1 wherein the bands extend across the sheet.

9. The patient restraint member of claim 1 wherein the spaces between the groups of perforations define the bands.

10. A patient restraint member for use in medical procedures, comprising:
    a partially perforated, integral, unitary sheet having an inner surface and an outer surface, with only a single layer of material between those surfaces, said material being formed of a thermoplastic material that can be softened upon heating so as to be formable into a shape corresponding to a patient's body part to be restrained and setting upon cooling to retain the shape, the sheet having a perimeter edge lying in a common plane and with the inner surface of the sheet arranged to directly engage the patient's body part to restrain movement of the patient's body part;
    at least one non-perforated band extending at least partially across the sheet to enhance rigidity of the sheet; and
    a generally planar U-shaped frame arranged to be attached to and extending around a portion of the perimeter edge of the sheet and being coplanar with the perimeter edge.

11. The patient restraint member of claim 10 wherein the at least one band extends perpendicular to the perimeter edge.

12. The patient restraint member of claim 10 the at least one band extends at a non-perpendicular angle to the perimeter edge.

13. The patient restraint member of claim 10 wherein the sheet has opposite side edges and opposite top and bottom edges, and wherein the edges are non-perforated.

14. The patient restraint member of claim 13 wherein the at least one band extends between the opposite side edges.

15. The patient restraint member of claim 10 wherein the at least one band extends completely across the sheet.

16. The patient restraint member of claim 10 further comprising a plurality of non-perforated bands extending inwardly from the perimeter edge.

17. The patient restraint member of claim 10 wherein the at least one band comprises plural bands which criss-cross the sheet.

* * * * *